(12) United States Patent
Kulessa

(10) Patent No.: US 7,896,865 B2  
(45) Date of Patent: Mar. 1, 2011

(54) TWO-COMPARTMENT REDUCED VOLUME INFUSION PUMP

(75) Inventor: Sigmund Kulessa, Newton, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 1447 days.

(21) Appl. No.: 10/676,326

(22) Filed: Sep. 30, 2003

(65) Prior Publication Data

US 2005/0070875 A1 Mar. 31, 2005

(51) Int. Cl.  
*A61K 9/22* (2006.01)

(52) U.S. Cl. ............... 604/890.1; 604/891.1; 604/65

(58) Field of Classification Search ........... 604/890.1, 604/891.1, 892.1, 65, 66  
See application file for complete search history.

(56) References Cited

U.S. PATENT DOCUMENTS

| | | | |
|---|---|---|---|
| 4,077,405 A | 3/1978 | Haerten et al. | |
| 4,193,397 A * | 3/1980 | Tucker et al. | 604/502 |
| 4,258,711 A | 3/1981 | Tucker et al. | |
| 4,955,861 A | 9/1990 | Enegren et al. | |
| 5,049,141 A | 9/1991 | Olive | |
| 5,360,407 A | 11/1994 | Leonard | |
| 5,395,324 A | 3/1995 | Hinrichs et al. | |
| 5,399,168 A | 3/1995 | Wadsworth, Jr. et al. | |
| 5,417,656 A | 5/1995 | Ensminger et al. | |
| 5,562,618 A | 10/1996 | Cai et al. | |
| 5,613,945 A | 3/1997 | Cai et al. | |
| 5,704,915 A | 1/1998 | Melsky et al. | |
| 5,743,873 A | 4/1998 | Cai et al. | |
| 5,792,104 A | 8/1998 | Speckman et al. | |
| 5,833,654 A | 11/1998 | Powers et al. | |
| 6,620,151 B2 * | 9/2003 | Blischak et al. | 604/891.1 |
| 2001/0048900 A1 | 12/2001 | Bardell et al. | |
| 2003/0040105 A1 | 2/2003 | Sklar et al. | |
| 2003/0133358 A1 * | 7/2003 | Karp | 366/341 |
| 2003/0171738 A1 | 9/2003 | Konieczynski et al. | |

FOREIGN PATENT DOCUMENTS

| | | |
|---|---|---|
| EP | 1342481 A | 9/2003 |
| EP | 1342481 A1 | 9/2003 |
| JP | 2000189514 A | 7/2000 |

OTHER PUBLICATIONS

European Search Report, European Patent Applicaton No. 04255994.8 dated Mar. 1, 2005 with Abstract in English.  
JP Office Action JP2004-284669 dated Mar. 2, 2010.

* cited by examiner

*Primary Examiner* — Nicholas D Lucchesi  
*Assistant Examiner* — Laura A Bouchelle

(57) ABSTRACT

An implantable infusion apparatus has a medication reservoir for storing a medication and a carrier reservoir for storing a carrier. The entire apparatus, including both reservoirs, is typically located in a housing made of stainless steel, titanium, or any other strong corrosion resistant biocompatible material. The medication and carrier reservoirs are accessed through a medication access port and a carrier access port, respectively. The access ports are covered with a medication compound septum and a carrier compound septum, respectively. The carrier reservoir is larger, and thus holds a larger volume, than the medication reservoir. To reduce the size of the implantable infusion apparatus, the medication is highly concentrated to many times the dosage required. The concentrated medication is then diluted with the carrier, to the proper dose, before it is discharged to the patient.

51 Claims, 9 Drawing Sheets

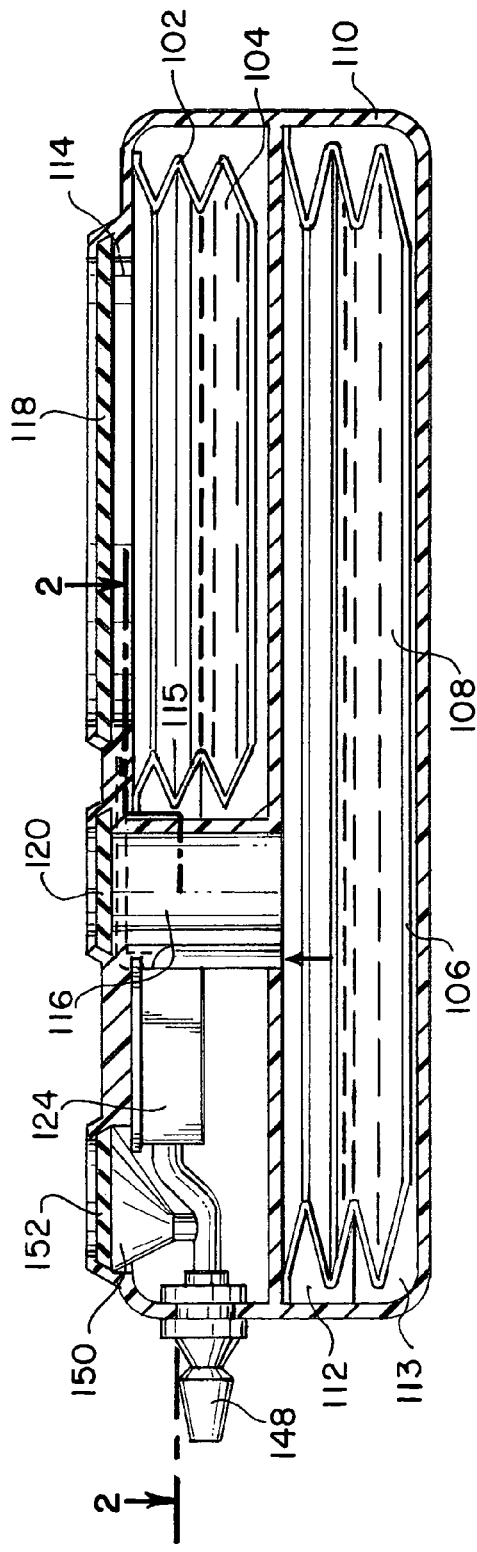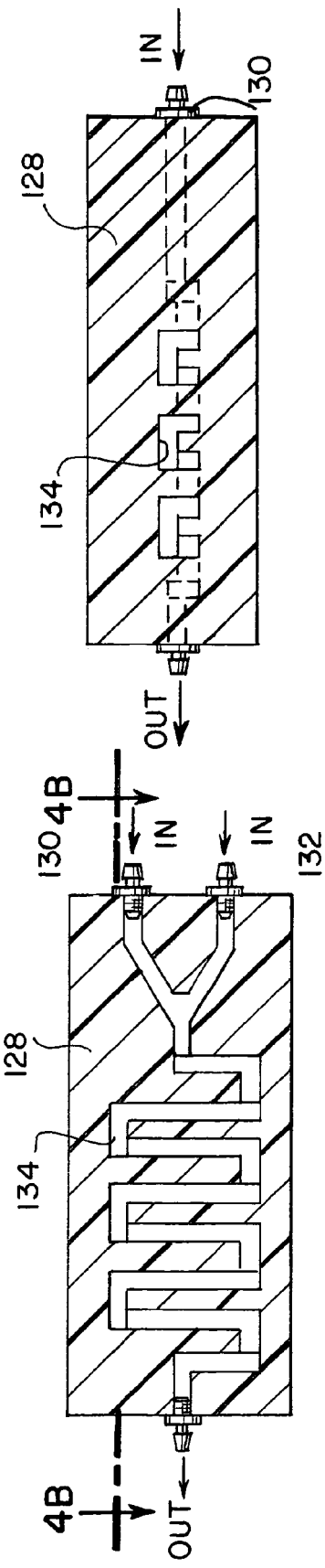

TWO-COMPARTMENT REDUCED VOLUME INFUSION PUMP

BACKGROUND OF THE INVENTION

1. Field of the Invention

This invention relates to an infusion pump apparatus and method wherein small amounts of concentrated medication are mixed and diluted with a carrier prior to being released into the patient. The use of a concentrated medication which is diluted will reduce the required size of the pump and the frequency of a patient's refill visits.

2. Discussion of the Related Art

Implantable access ports and drug infusion pumps are well known in the art. For example, U.S. Pat. No. 5,792,104 to Speckman et al. and U.S. Pat. No. 5,833,654 to Powers et al. both disclose dual reservoir access ports. However, the ports of both Speckman and Powers are designed so that the contents of the reservoirs are never mixed, either internal or external to the ports. Both Speckman and Powers disclose attachment means and dual lumen catheters that are designed to keep the contents of the reservoirs separate until the catheter discharges into the patient. Thus, neither Speckman nor Powers allows for the contents of the reservoirs to be mixed prior to discharge to the patient.

Tucker et al. in U.S. Pat. Nos. 4,193,397 and 4,258,711 (hereinafter "Tucker") disclose a dual reservoir implantable pump with an accumulator. Tucker further discloses a basal reservoir containing medication of a certain dosage and a smaller bolus reservoir containing high concentrate medication. The basal reservoir discharges medication to the patient at a specified rate. The basal reservoir discharges the high concentration of medication to a smaller accumulator and, at a specified time, the accumulator discharges the bolus dose into the basal medication discharge. However, Tucker's bolus dose is never mixed and diluted with the basal dose. The bolus dose is sent as a short 'burst' of medication at timed or triggered intervals. Additionally, both the basal and the bolus reservoirs contain medication that must be refilled by a doctor.

Thus, there is a need in the art for an implantable infusion device that mixes and dilutes a non-medication carrier with concentrated medication to reduce the size of the device. Additionally, diluting a concentrated medication with a carrier allows a patient to refill his/her own carrier reservoir multiple times before the medication reservoir requires refilling. This reduces the number of times a patient must visit a doctor to refill the medication reservoir.

SUMMARY OF THE INVENTION

An implantable infusion apparatus has a medication reservoir for storing a medication and a carrier reservoir for storing a carrier. The entire apparatus, including both reservoirs, is typically located in a single housing. The housing can be made of stainless steel, titanium, or any other strong corrosion resistant material. The reservoirs are typically made in the form of a bellows that expands and contracts with the discharge and replenishment of the liquid inside. The medication reservoir and the carrier reservoir are accessed through a medication access port and a carrier access port, respectively. The access ports are covered with a medication compound septum and a carrier compound septum, respectively. Both compound septa are formed from elastomeric, needle-penetrable, self-sealing material that enables needles to access the reservoirs. Additionally, access to the reservoirs can be gained through any number of valve, needle, and needle stop configurations as known in the art. Further, tactile ridges can be formed on the housing around the access ports to allow a doctor, nurse, or patient to locate the access ports by palpating the skin. Once the tactile ridges are located, it is immediately known where the medication and carrier compound septa are located below the skin. The placement and shape of the ridges are well known by those of skill in the art.

The carrier reservoir is larger and thus holds a larger volume than the medication reservoir. To reduce the size of the implantable infusion pump apparatus, the medication is highly concentrated to many times the dosage required. The concentrated medication is then diluted with the carrier to the proper dose, before it is discharged into the patient. The carrier is typically saline or other sterile liquid carrier. The carrier reservoir can be about 4 to about 5 times the size as the medication reservoir.

BRIEF DESCRIPTION OF THE DRAWINGS

The above and still further objects, features and advantages of the present invention will become apparent upon consideration of the following detailed description of a specific embodiment thereof, especially when taken in conjunction with the accompanying drawings wherein like reference numerals in the various figures are utilized to designate like components, and wherein:

FIG. 3 is a is a cross-section along line 3-3 of FIG. 1;

FIG. 4A is a top view of a microfluidic chip;

FIG. 4B is a cross-sectional view along line 4B-4B of FIG. 4A;

DETAILED DESCRIPTION OF THE PREFERRED EMBODIMENT

Figure 1:
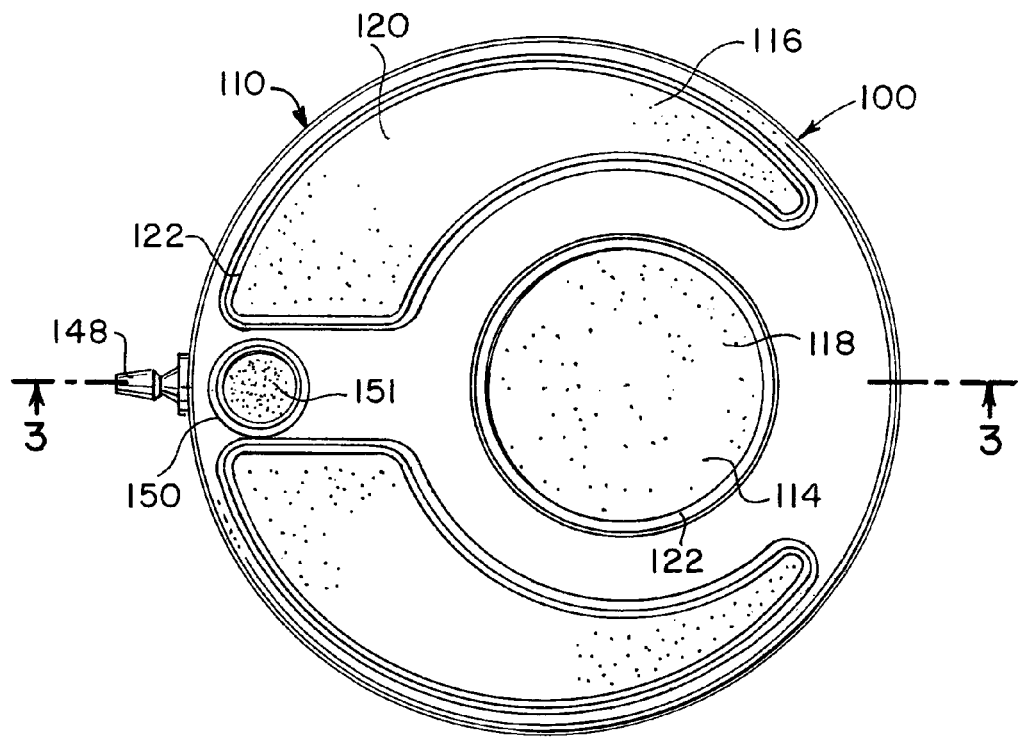
FIG. 1 is a top view of the implantable infusion apparatus of the present invention.
Figure 2:
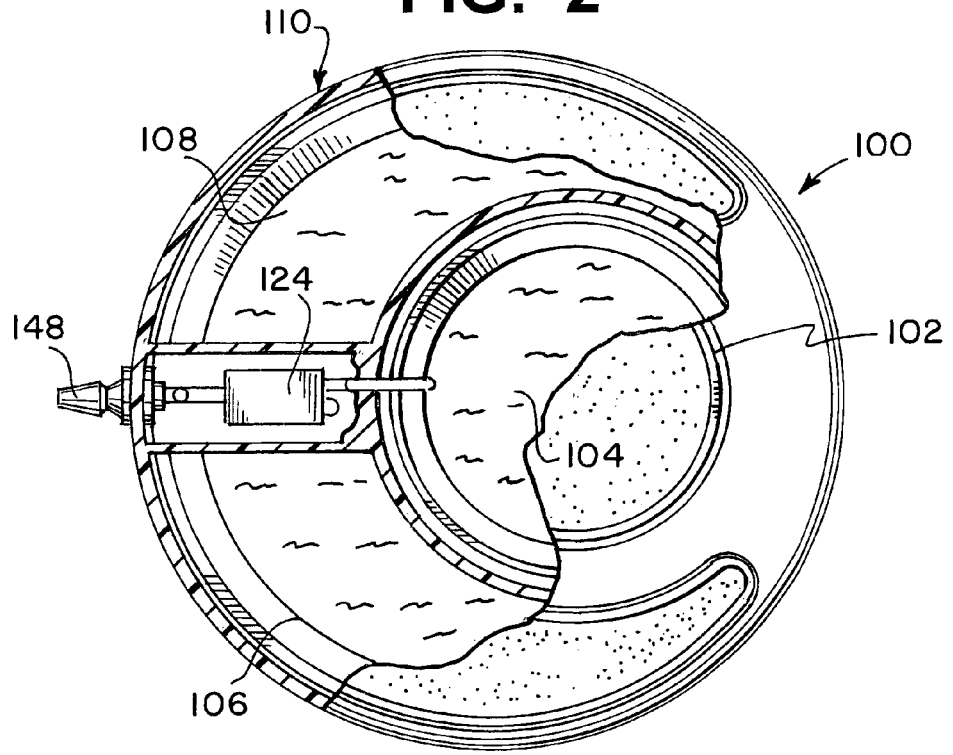
FIG. 2 is a partial cut-away view of the pump of along line 2 of FIG. 3.

Referring now to FIGS. 1 and 2, an implantable infusion apparatus 100 in accordance with the present invention is illustrated. FIG. 2 illustrates a medication reservoir 102 for storing a medication 104 and a carrier reservoir 106 for storing a carrier 108. The entire apparatus, including both reservoirs, is typically located in a housing 110. Housing 110 can be made of stainless steel, titanium, or any other strong corrosion-resistant, biocompatible material. The reservoirs are typically in the form of a bellows 112 (FIG. 3) that expands and contracts with the discharge and replenishment of the liquid inside. FIG. 1 illustrates that medication reservoir 102 and carrier reservoir 106 are accessed through a medication access port 114 and a carrier access port 116, respectively. Access ports 114, 116 are covered with a medication compound septum 118 and a carrier compound septum 120, respectively. Both compound septa 118, 120 are formed from elastomeric, needle-penetrable, self-sealing material that enables needles to access the reservoirs. Additionally, access to reservoirs 102, 106 can be gained through any number of valve, needle, and needle stop configurations as known in the art. Further, tactile ridges 122 can be formed on the housing around access ports 114, 116 to allow a doctor, nurse, or patient to locate access ports 114, 116 by palpating the skin. Once tactile ridges 122 are located, it is immediately known where medication compound septum 118 and carrier compound septum 120 are located below the skin. The placement and shape of the ridges are well known by those of skill in the art.

FIGS. 2 and 3 illustrate that carrier reservoir 106 is larger than medication reservoir 102. To reduce the size of implantable infusion apparatus 100, medication 104 is highly concentrated to many times the dosage required. Concentrated medication 104 is then diluted with carrier 108 before it is discharged to the patient. Carrier 108 is typically saline or other sterile liquid carrier. Carrier reservoir 106 can be about 4 to about 5 times the size as medication reservoir 102. For example, carrier reservoir 106 can hold 20 ml and the medication can be about 4 ml or about 5 ml and the above arrangement can replace one 40 ml reservoir.

In addition to reducing the size of the implantable infusion apparatus, the invention can reduce or shorten the number or length of a patient's doctor visits. Typically, only a doctor can refill medication reservoir 102. But, because medication 104 is highly concentrated and then diluted with carrier 108, the doctor will not be required to fill medication reservoir 102 as often. Carrier reservoir 106 is only filed with a non-medication substance. Since carrier 108 is not a medication, either the patient at home, or a nurse can refill carrier reservoir 106. In one embodiment, carrier compound septum 120 is larger and/or differently shaped than the medication compound septum 118 to assist the patient in locating carrier reservoir 106. An alternate embodiment can provide a single access port for both reservoirs wherein only a particular type of needle (e.g. by length or location of the discharge orifice) can access each of the reservoirs. The above safeguards can allow a patient to safely refill carrier reservoir 106. The location of access ports 114, 116 with respect to pump housing 110 can also assist the patient/nurse/doctor in distinguishing between carrier access port 116 and medication access port 114. For example, medication access port 114 can be disposed in the center of housing 110 and carrier access port 116 can be disposed along housing's 110 perimeter.

A mixing chamber 124 is included to thoroughly mix and dilute medication 104 with carrier 108. Mixing chamber 124 must allow for full dilution and mixing of carrier 108 with medication 104 or the patient will receive an improper dose. One embodiment, as illustrated in FIGS. 4A and 4B, uses a microfluidic chip 128 to mix the two substances. Microfluidic chip 128 can have a medication input 130 and a carrier input 132 and capillary pathway 134 is configured in a serpentine pattern. The capillary pathway 134 can include convolutions in vertical and horizontal planes to the direction of flow. The convolutions act to allow medication 104 sufficient contact time with carrier 108 to allow for thorough mixing. Examples of microfluidic mixing chips include U.S. Patent Publication No. 2001/0048900, to Bardell et al.; U.S. Patent Publication No. 2003/0040105 to Sklar et al.; and U.S. Patent Publication No. 2003/0133358 to Karp. Other microfluidic mixing chips and mixing chambers to allow for thorough mixing are known to those of skill in the art.

One key to the mixing process is controlling the flow of both medication 104 and carrier 108 from reservoirs 102, 106 to mixing chamber 124. The flow rate can be controlled in numerous ways described below.

Figure 4C:
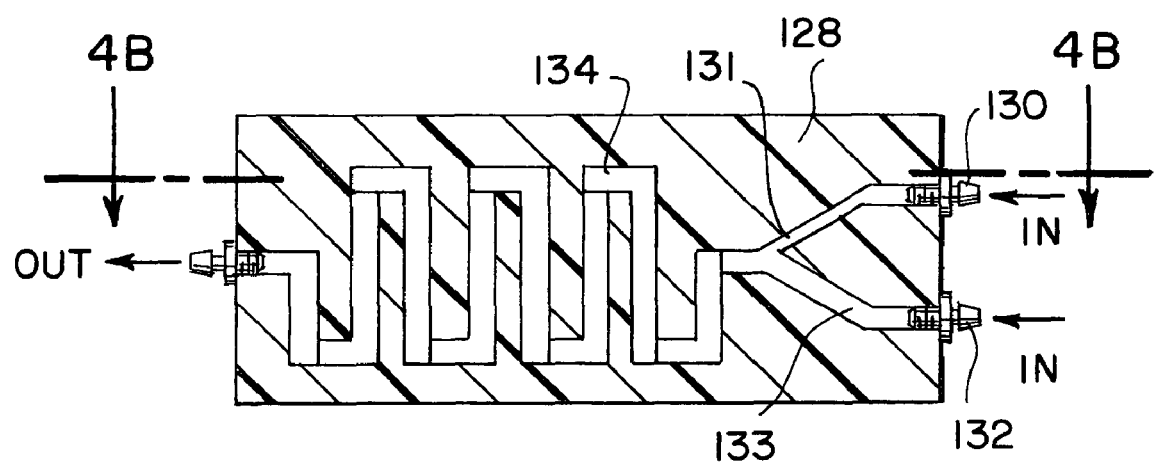
FIG. 4C is a top view of an alternate embodiment of the microfluidic chip.
Figure 5:
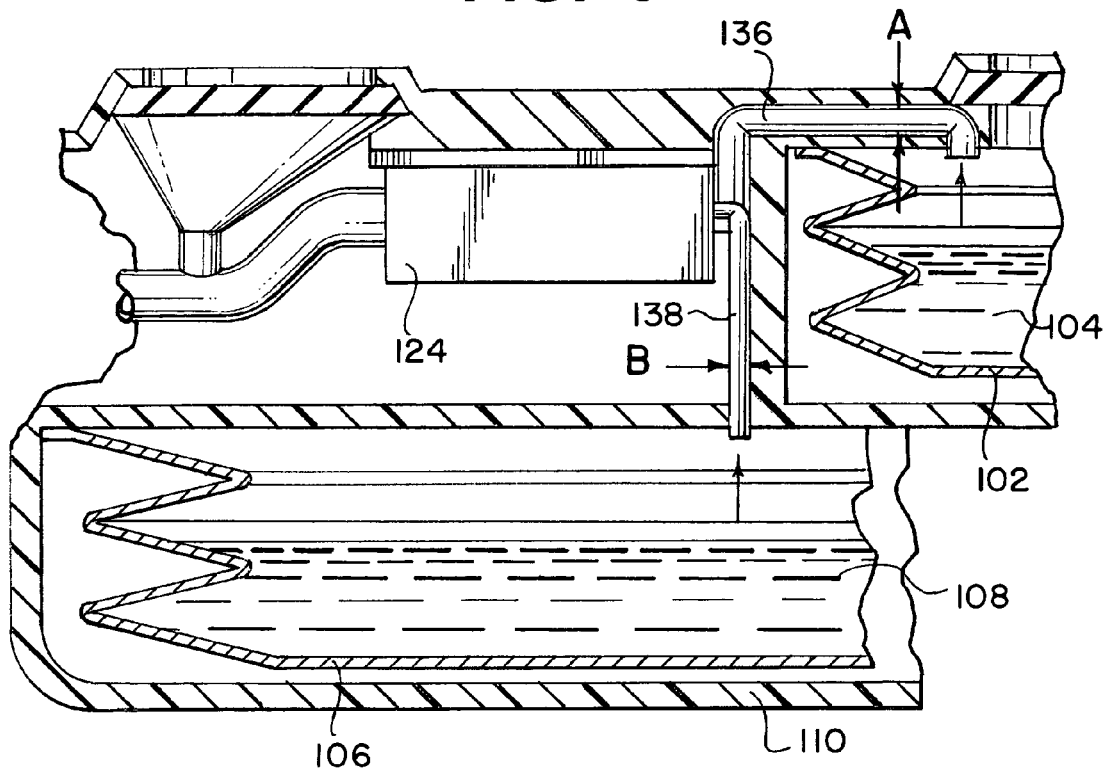
FIG. 5 is a magnified view of one embodiment of the flow paths of the present invention.
Figure 6:
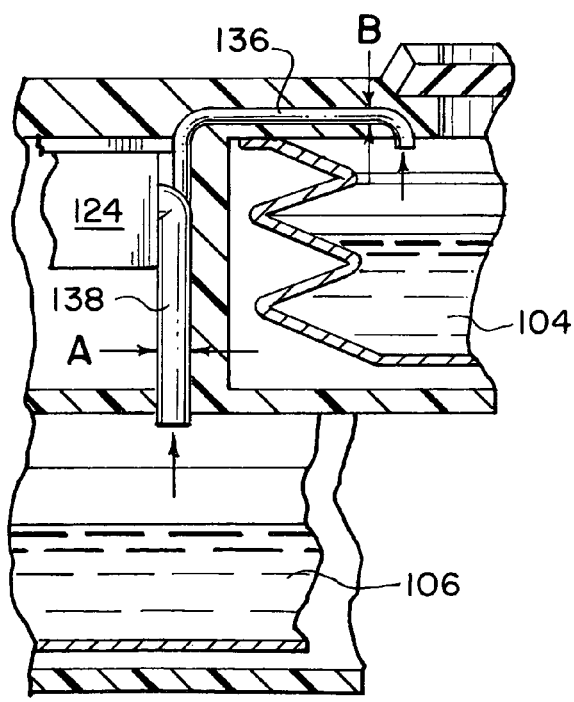
FIG. 6 is a magnified view of another flow path embodiment of the present invention.

Referring now to FIGS. 5 through 9, a medication flow path 136 fluidly connects medication reservoir 102 to mixing chamber 124 and a carrier flow path 138 fluidly connects carrier reservoir 106 to mixing chamber 124. The flow paths can simply act as conduits between the reservoirs and the mixing chamber. FIG. 5 illustrates one embodiment that alters the physical properties of medication flow path 136 so it is less restrictive than carrier flow path 138. Conversely, FIG. 6 illustrates that medication flow path 136 is more restrictive than carrier flow path 138. The restrictive nature of a flow path is a factor in determining the flow rate of the fluid inside the path. For example, as illustrated in FIG. 5, medication flow path 136 can be designed with a larger diameter A than a smaller diameter B of carrier flow path 138. FIG. 6 illustrates that larger diameter A of carrier flow path 138 can be larger than smaller diameter B of medication flow path 136. The restrictions in the flow path can also be built into microfluidic chip 128, after inputs 130, 132, and before mixing chamber 124. FIG. 4C illustrates a medication reduced diameter section 131, internal to microfluidic chip 128 that can act as the restriction to flow. Alternately, a carrier reduced diameter section 133 can also be disposed internal to microfluidic chip 128 to restrict the flow of carrier 108. FIG. 4C illustrates both medication and carrier reduced diameter sections 131, 133, however, the reduced diameter sections can be used together or only one section can be restricted.

Figure 7:
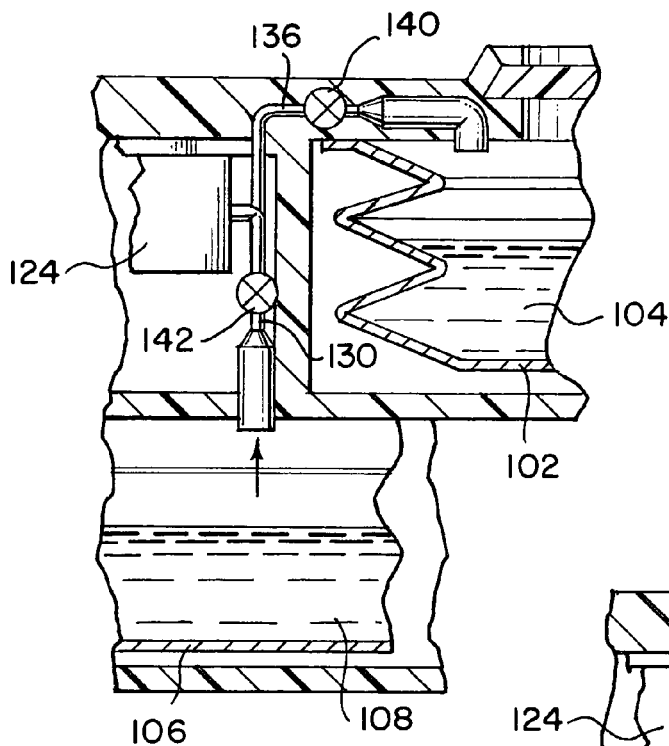
FIG. 7 is a magnified view of a restricted flow path embodiment of the present invention.
Figure 8:
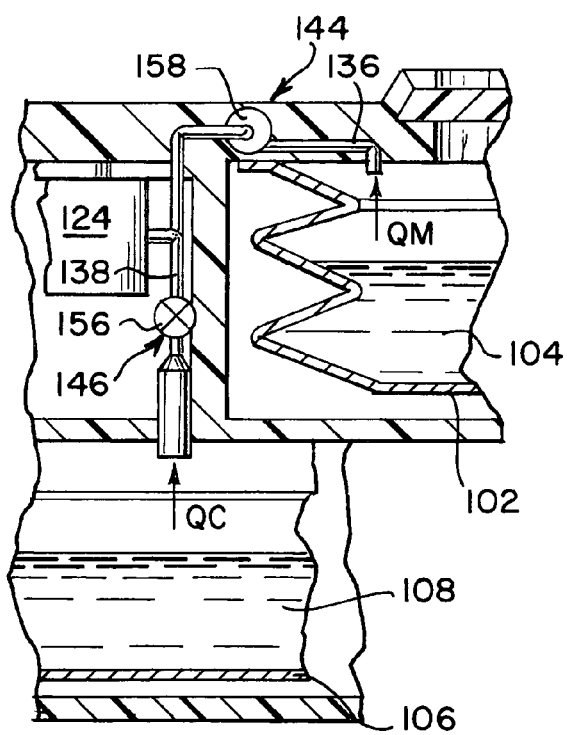
FIG. 8 is a magnified view of the medication flow selector of the present invention.
Figure 9:
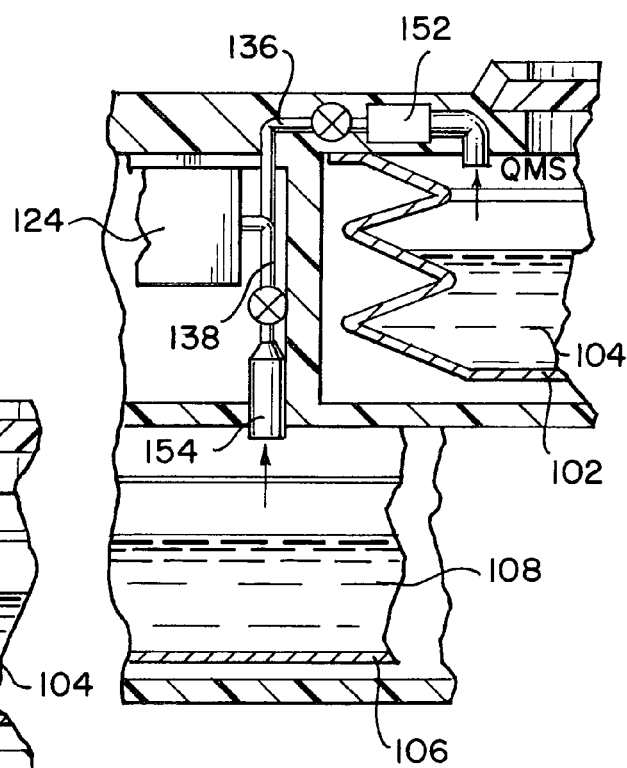
FIG. 9 is a magnified view of another flow path of the present invention.

Additional embodiments, as illustrated in FIGS. 7 through 9, dispose either a medication flow restrictor 140 in medication flow path 136 to restrict the flow of medication 104 between medication reservoir 102 and mixing chamber 124; a carrier flow restrictor 142 in carrier flow path 138 to restrict the flow of carrier 108 between carrier reservoir 106 and mixing chamber 124; or both flow restrictors 140, 142 can be included in the same apparatus, as illustrated in FIG. 7. Flow restrictors 140, 142 can be physical changes to flow paths 136, 138 or microfluidic chips (not illustrated), depending on the configuration and flow rate required. As above, either flow restrictor 140, 142 can be more or less restrictive than the other.

Referring to FIG. 8, a medication pump system 144 is used to discharge medication 104 to mixing chamber 124 and a carrier pump system 146 is used to discharge carrier 108 to mixing chamber 124. Medication pump system 144 has a medication discharge rate Qm and carrier pump system 146 has a carrier discharge rate Qc. As above, to properly control the mixing of medication 104 with carrier 108, the proper flows must be determined so the proper amount of medication 104 is diluted with the proper amount of carrier 108, depending on the dose to be administered to the patient. Discharge rates Qm, Qc can be configured in many ways, for example, medication discharge rate Qm can equal carrier discharge rate Qc and the flow can be restricted down stream of the pump by either flow paths 136, 138 or flow restrictors 140, 142. Alternately, medication discharge rate Qm can be greater than or less than carrier discharge rate Qc or any combination of flow paths 136, 138, flow restrictors 140, 142 and discharge rates Qm, Qc can be used to control the flow of both carrier 108 and medication 104.

Pump systems 144, 146 can be any pumping system known to those of skill in the art, including a power cell 113, 115 associated with the medication and the carrier reservoirs, respectively. Power cells 113, 115 can be a two-phase fluid power cell, where the fluid in the power cell vaporizes at physiological temperatures. The gas formed from the vaporization of the fluid forces the reservoir to contract and expel the medication or carrier contained therein. When the reservoir is refilled, the reservoir is forced to expand against the vaporized liquid and the vaporized liquid condenses. Another power cell 113, 115 embodiment pressurizes the area surrounding medication and carrier reservoirs 102, 106 with a propellant, such as butane or Freon. The positive pressure of the propellant forces fluid out of reservoirs 102, 106 through one or both flow restrictors 140, 142 or microfluidic restrictors 131, 133. The combination of constant pressure and constant fluidic resistance due to the restrictors results in a constant discharge rates Qm, Qc. Additionally, a traditional battery operated system can be used to discharge medication 104 and carrier 108.

An outlet port 148 (FIGS. 1 and 10) is fluidly connected to mixing chamber 124 for discharging a diluted medication/carrier mixture to the patient. Outlet port 148 can be positioned and configured numerous ways to connect to a catheter (not illustrated) leading anywhere in the body.

Figure 10:
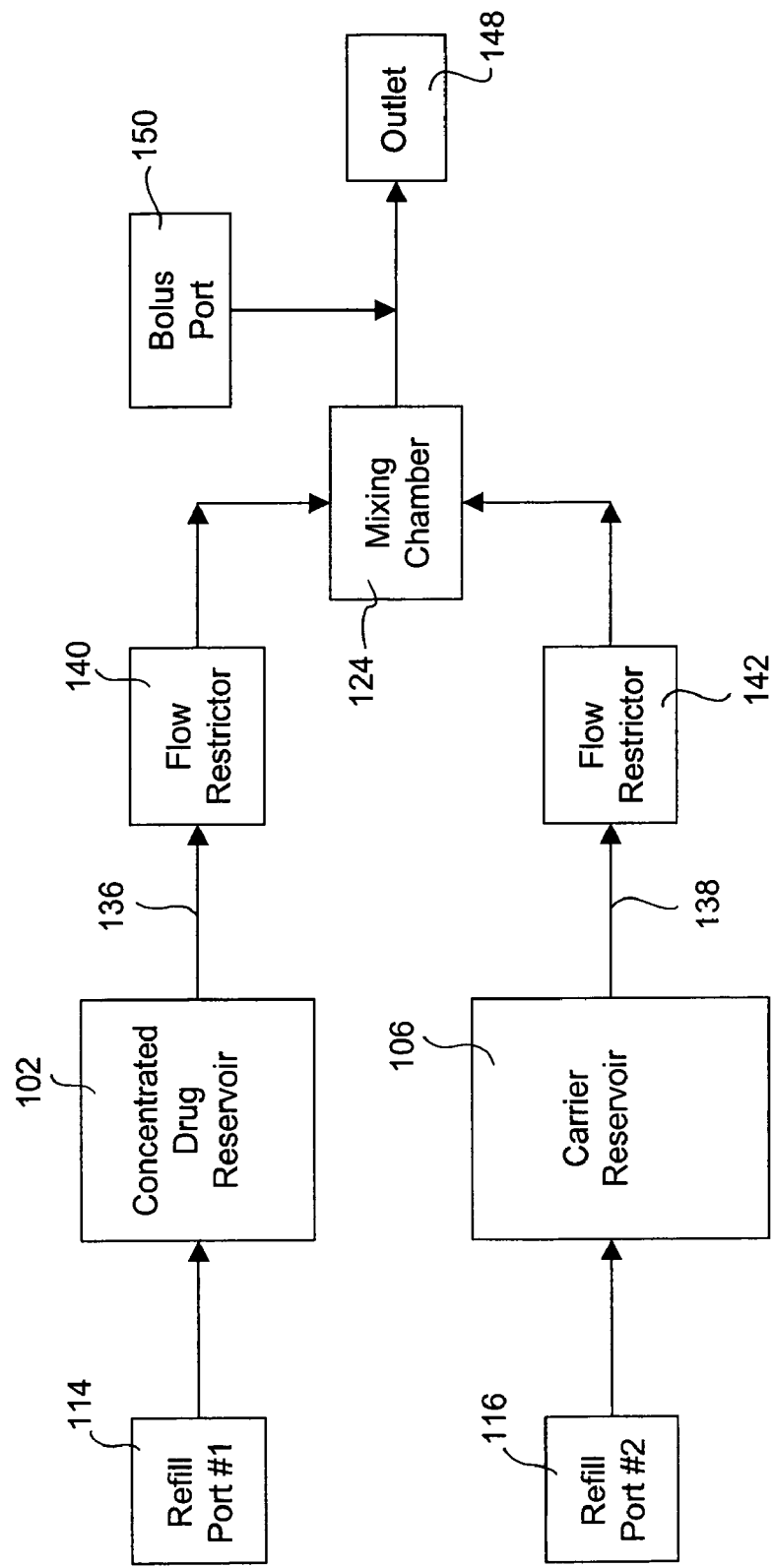
FIG. 10 is a schematic flow diagram illustrating a flow path of the present invention.

The embodiment of implantable infusion apparatus 100 shown in FIG. 10 further includes a bolus port 150 disposed between mixing chamber 124 and outlet port 148. Bolus port 150 allows a doctor to introduce a bolus dose into apparatus 100, after medication 104 and carrier 108 have been mixed, but prior to the diluted mixture being discharged from apparatus 100. Bolus port 150 can be covered by a bolus compound septum 151 (FIG. 1) made of similar material to the septa described above. Additionally, bolus port 150 can be accessed from a common access port shared with the reservoirs and configured for another type of needle.

Referring now to FIG. 9, another embodiment of an implantable infusion apparatus 100 is illustrated. FIG. 9 illustrates an electronically controlled medication flow selector 152 disposed in medication flow path 136 for controlling a selected medication discharge rate Qms of medication 106 to mixing chamber 124. Using medication flow selector 152, a doctor can alter the dosage of medication a patient receives without completely draining medication 104 from medication reservoir 102 and replacing it with a higher or lower concentration of medication 104. By altering the flow, a doctor can control how much medication 104 is mixed with carrier 108, and thus control the dosage. Another embodiment utilizes a carrier flow selector 154 disposed in carrier flow path 138 for controlling a selected carrier discharge rate Qcs of carrier 108 to mixing chamber 124. Controlling the discharge rate of the carrier also affects the dosage. Both medication flow selector 152 and carrier flow selector 154 can be made of a valve 156 or a pump 158 (FIGS. 8 and 9). An electronic device, such as a timer or a remote control, can control either valve 156 or pump 158. Flow selector 152 can be set to increase or decrease the amount of medication 104 that enters mixing chamber 124 based on a preset time. Additionally, telemetric remote controls can alter the programming of flow selectors 152, 154 through the skin of the patient. All of the other elements of the implantable infusion apparatus containing medication flow selector 152 are similar to the elements described in the above embodiments. Thus, embodiments of implantable infusion apparatus 100 include constant flow, wherein the flow rates of both the medication and the carrier are fixed prior to implanting the infusion apparatus into the patent; programmable flow, wherein the infusion apparatus contains electronics that are programmed to alter the flow of the medication and/or the carrier to vary the dosage to the patent at different times; and adjustable flow models that provide a constant flow of the medication and carrier but the medication and/or carrier flow rate can be adjusted by a doctor to alter the flow rate of the constant flow.

Figure 11:
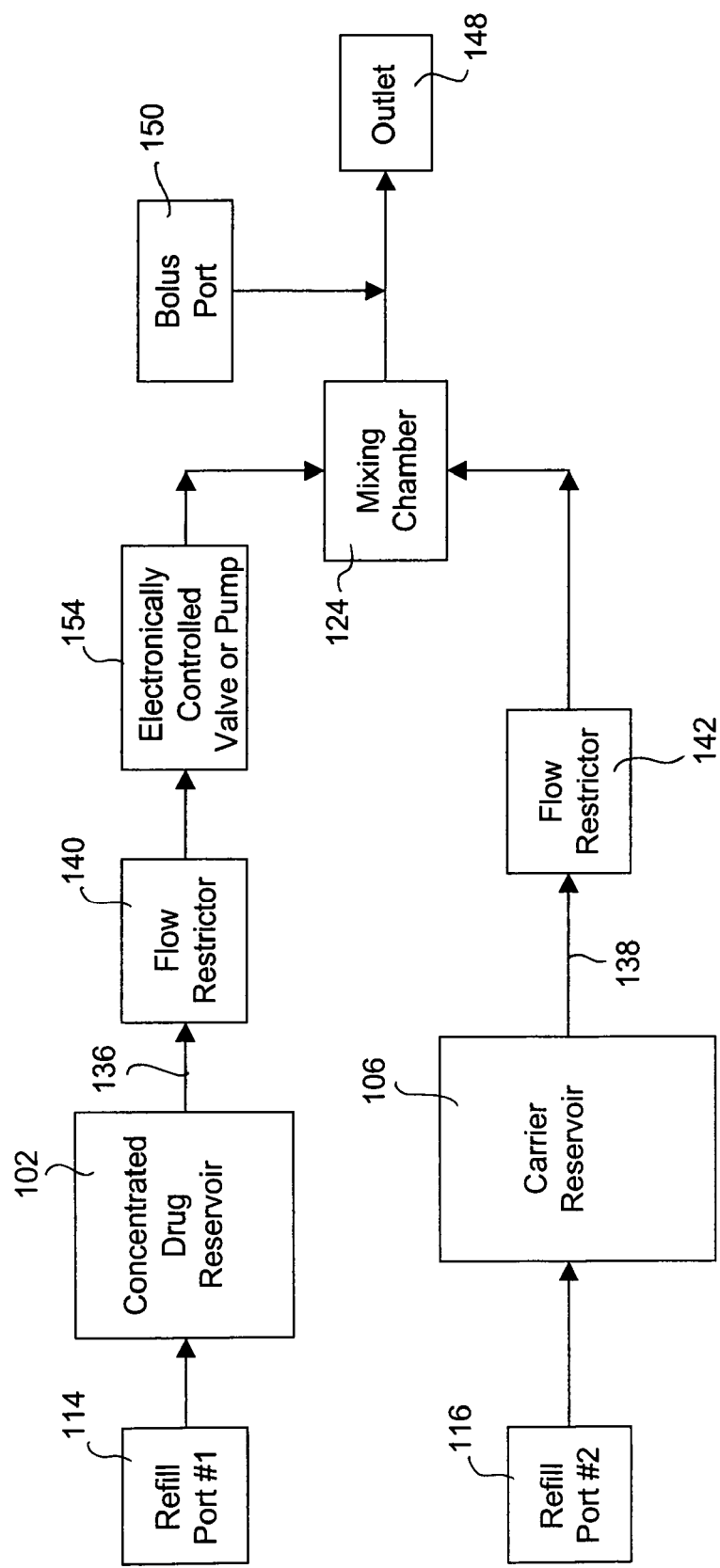
FIG. 11 is a schematic flow diagram illustrating another flow path of the present invention.

FIGS. 10 and 11 are schematic diagrams illustrating typical embodiments for the present invention. FIG. 10 schematically illustrates medication access port 114 in-line with medication reservoir 102. Medication flow path 136 fluidly connects medication reservoir 102 to mixing chamber 124 via medication flow restrictor 140. Carrier access port 116 is fluidly connected to carrier reservoir 106 and carrier flow path 138 fluidly connects carrier reservoir 106 to mixing chamber 124 via carrier flow restrictor 142. Further, bolus port 150 is disposed in the flow path between mixing chamber 124 and outlet 148 to permit the injection of a bolus dose. FIG. 11 illustrates another embodiment wherein medication flow selector 154 is located in the flow path between medication flow restrictor 140 and mixing chamber 124 to allow additional control of medication discharge rate Qm.

Figure 12:
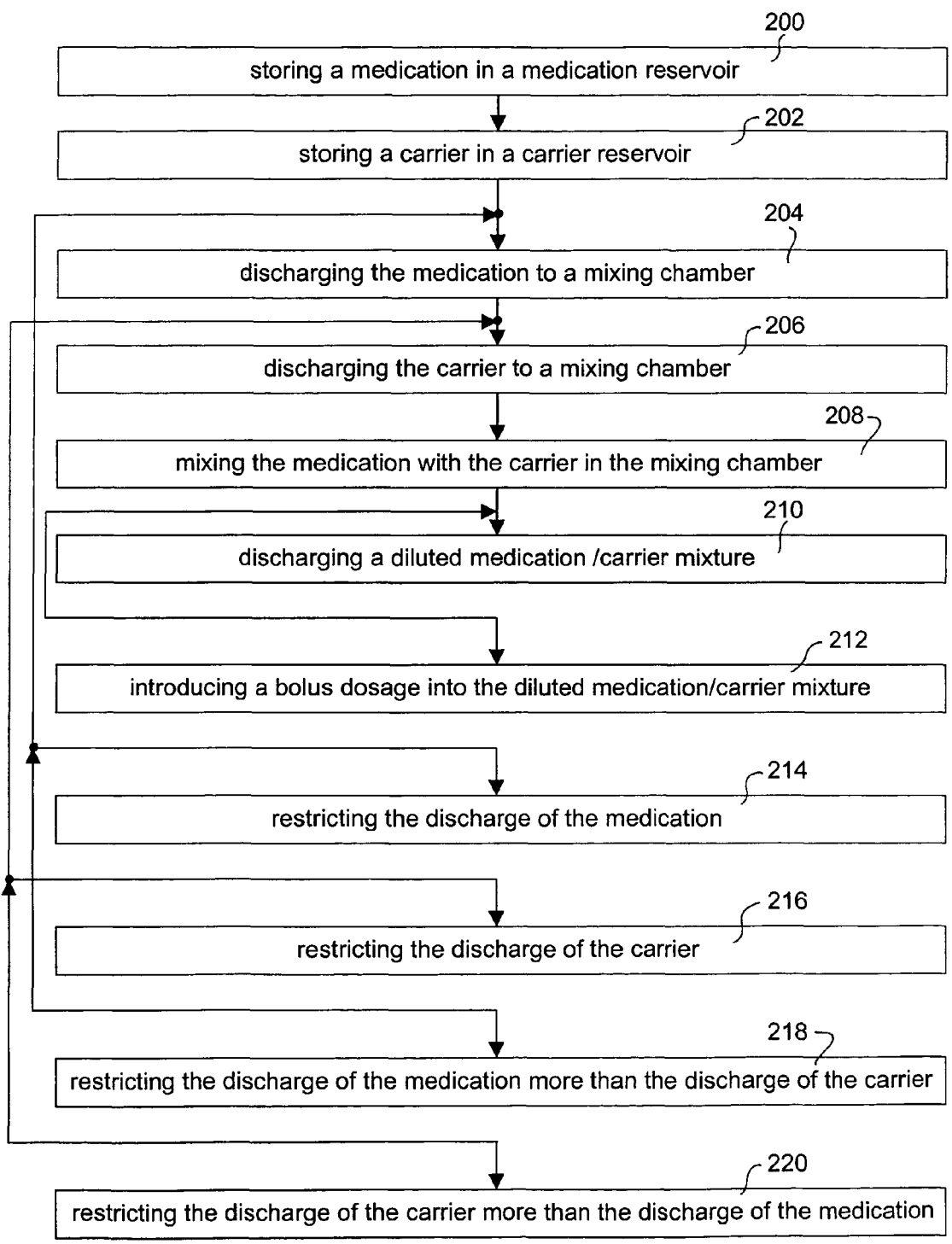
FIG. 12 is a flow chart illustrating a method of infusing medication according to the present invention.

FIG. 12 illustrates a method of infusing medication including storing a medication in a medication reservoir (step 200) and storing a carrier in a carrier reservoir (step 202). The carrier reservoir is sized larger than the medication reservoir. Approximately simultaneously, the medication is discharged to a mixing chamber (step 204) and the carrier is discharged to the mixing chamber (step 206). Once in the mixing chamber, the medication is mixed with the carrier to dilute it (step 208); and then the diluted medication/carrier mixture is discharged (step 210). As an additional step, a bolus dosage may be introduced into the diluted medication/carrier mixture prior to discharging the diluted medication/carrier mixture (step 212).

Another embodiment can restrict the discharge of the medication (step 214), restrict the discharge of the carrier (step 216) or restrict both. When both the medication and the carrier are restricted, the discharge of the medication can be restricted more than the discharge of the carrier (step 218) or the carrier can be more restricted than the discharge of the medication (step 220). Other embodiments restrict the discharge of both the medication and the carrier to a certain extent to provide a constant flow rate to counter the constant action of the pumping system.

Figure 13:
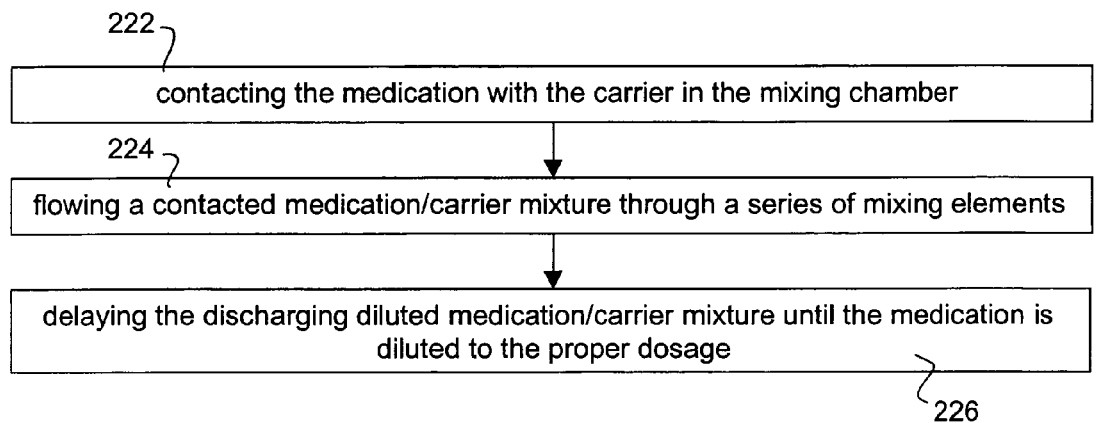
FIG. 13 is a flow chart illustrating another method of infusing medication according to the present invention.

Further, FIG. 13 illustrates that the dilution step can include contacting the medication with the carrier in the mixing chamber (step 222); flowing the contacted medication/carrier mixture through a series of mixing elements (step 224); and delaying the discharging of the diluted medication/carrier mixture until the medication is diluted to the proper dosage (step 226). The mixing elements can be baffles, hydraulic turbulence, or other mixing elements found in microfluidic devices.

Figure 14:
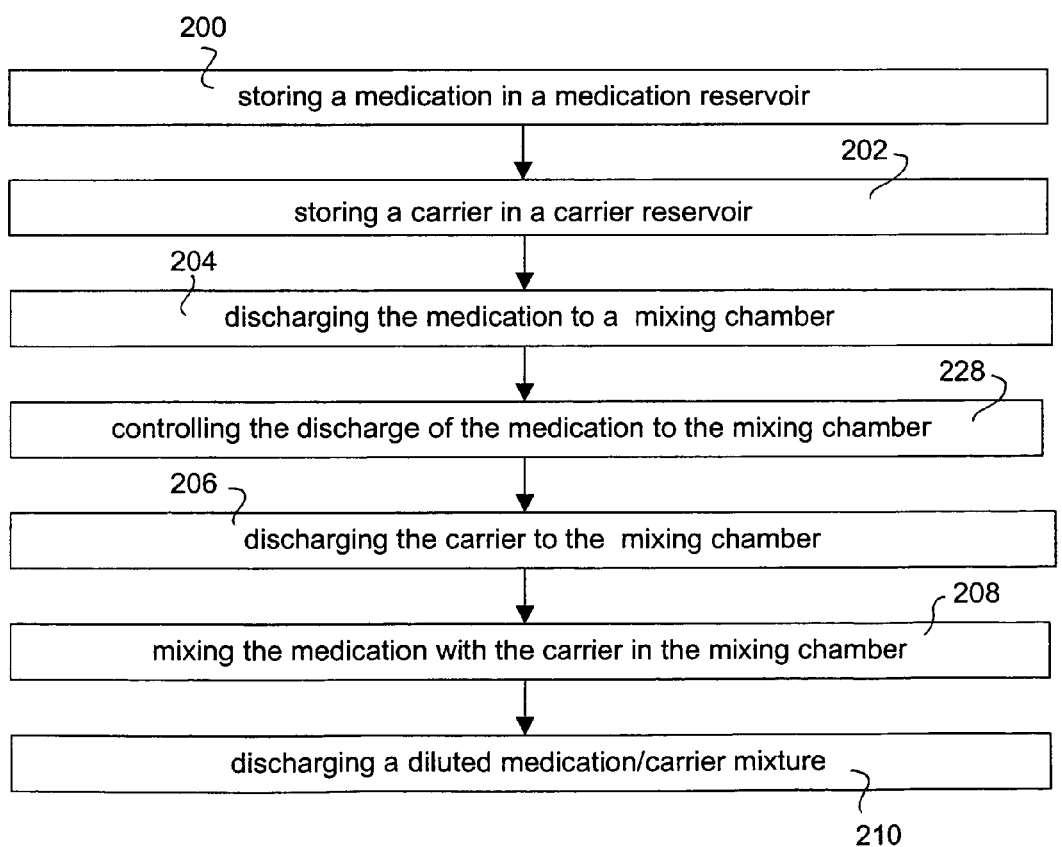
FIG. 14 is a flow chart illustrating another embodiment for infusing medication.

FIG. 14 illustrates another embodiment that adds the step of controlling the discharge of the medication into the mixing chamber (step 228). The electronic flow selectors as described above can perform the step of controlling the discharge of the medication.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps which perform substantially the same function, in substantially the same way, to achieve the same results are within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

What is claimed is:

1. An infusion apparatus implantable in a human body, comprising:
   a medication reservoir for storing a medication;
   a carrier reservoir for storing a carrier, wherein the carrier reservoir is larger than the medication reservoir;
   a mixing chamber in which the medication and carrier are thoroughly mixed, thus diluting the medication with the carrier, said mixing chamber being a micro fluidic chip having a capillary pathway disposed in a serpentine pattern;
   a medication flow path fluidly connecting the medication reservoir to the mixing chamber;
   a carrier flow path fluidly connecting the carrier reservoir to the mixing chamber;
   a medication pump system for discharging the medication to the mixing chamber;
   a carrier pump system for discharging the carrier to the mixing chamber;
   an outlet port fluidly connected to the mixing chamber for discharging a diluted medication/carrier mixture; and
   a bolus port disposed between the mixing chamber and the outlet port.

2. The implantable infusion apparatus of claim 1, further comprising:
   a medication flow restrictor disposed in the medication flow path to restrict a flow of the medication between the medication reservoir and the mixing chamber.

3. The implantable infusion apparatus of claim 2, wherein the medication flow restrictor is a micro fluidic chip.

4. The implantable infusion apparatus of claim 1, further comprising:
   a carrier flow restrictor disposed in the carrier flow path to restrict a flow of the carrier between the carrier reservoir and the mixing chamber.

5. The implantable infusion apparatus of claim 4, further comprising:
   a medication flow restrictor disposed in the medication flow path to restrict a flow of the medication between the medication reservoir and the mixing chamber.

6. The implantable infusion apparatus of claim 4, wherein the carrier flow restrictor is a microfluidic chip.

7. The implantable infusion apparatus of claim 5, wherein the medication flow restrictor is more restrictive than the carrier flow restrictor.

8. The implantable infusion apparatus of claim 5, wherein the medication flow restrictor is less restrictive than the carrier flow restrictor.

9. The implantable infusion apparatus of claim 1, wherein the medication flow path is more restrictive than the carrier flow path.

10. The implantable infusion apparatus of claim 1, wherein the medication flow path is less restrictive than the carrier flow path.

11. The implantable infusion apparatus of claim 1, wherein the medication pump system has a medication discharge rate and the carrier pump system has a carrier discharge rate, and the medication discharge rate is greater than the carrier discharge rate.

12. The implantable infusion apparatus of claim 1, wherein the medication pump system has a medication discharge rate, and the carrier pump system has a carrier discharge rate and the medication discharge rate is less than the carrier discharge rate.

13. The implantable infusion apparatus of claim 1, wherein the medication pump system and the carrier pump system comprises a power cell selected from the group consisting of a two-phase fluid power cell associated with the medication and the carrier reservoirs, the fluid in the power cell vaporizing at physiological temperatures and a gas pressurized power cell charged with a propellant.

14. The implantable infusion apparatus of claim 1, wherein the medication pump system and the carrier pump system comprises a battery operated system.

15. The implantable infusion apparatus of claim 1, further comprising a housing enclosing the implantable infusion apparatus wherein the housing is sized to be implantable in the human body.

16. The implantable infusion apparatus of claim 1, further comprising:
   a medication access port to access the medication reservoir and covered with a medication compound septum; and
   a carrier access port to access the carrier reservoir and covered with a carrier compound septum.

17. An implantable infusion apparatus comprising:
   a medication reservoir for storing a medication;
   a carrier reservoir for storing a carrier, wherein the carrier reservoir is larger than the medication reservoir;
   a mixing chamber in which the medication may be mixed with and diluted by the carrier, said mixing chamber being a microfluidic chip having a capillary pathway disposed in a serpentine pattern;
   a medication flow path fluidly connecting the medication reservoir to the mixing chamber;
   a carrier flow path fluidly connecting the carrier reservoir to the mixing chamber;
   a medication pump system for discharging the medication into the mixing chamber;
   a carrier pump system for discharging the carrier into the mixing chamber;
   an electronically controlled medication flow selector disposed in the medication flow path for controlling a discharge rate of the medication to the mixing chamber;
   an outlet port fluidly connected to mixing chamber for discharging a diluted medication/carrier mixture; and
   a bolus port disposed between the mixing chamber and the outlet port.

18. The implantable infusion apparatus of claim 17, wherein the medication flow selector is one of a valve and a pump.

19. The implantable infusion apparatus of claim 17, wherein the medication flow selector further comprises a controller for altering the medication discharge rate.

20. The implantable infusion apparatus of claim 17, further comprising:
   an electronically controlled carrier flow selector disposed in the carrier flow path for controlling a discharge rate of the carrier to the mixing chamber.

21. The implantable infusion apparatus of claim 20, wherein the carrier flow selector is one of a valve and a pump.

22. The implantable infusion apparatus of claim 20, wherein the carrier flow selector further comprises a controller for altering the carrier discharge rate.

23. The implantable infusion apparatus of claim 17, further comprising:
   a medication flow restrictor disposed in the medication flow path prior to the medication flow selector for restricting the flow of the medication between the medication reservoir and the mixing chamber.

24. The implantable infusion apparatus of claim 23, further comprising:
a medication flow restrictor disposed in the medication flow path prior to the medication flow selector to restrict the flow of the medication between the medication reservoir and the medication flow selector.

25. The implantable infusion apparatus of claim 23, wherein the medication flow restrictor is a micro fluidic chip.

26. The implantable infusion apparatus of claim 17, further comprising:
a carrier flow restrictor disposed in the carrier flow path to restrict the flow of the carrier between the carrier reservoir and the mixing chamber.

27. The implantable infusion apparatus of claim 26, wherein the medication flow restrictor is more restrictive than the carrier flow restrictor.

28. The implantable infusion apparatus of claim 26, wherein the medication flow restrictor is less restrictive than the carrier flow restrictor.

29. The implantable infusion apparatus of claim 26, wherein the carrier flow restrictor is a microfluidic chip.

30. The implantable infusion apparatus of claim 17, wherein the medication flow path is more restrictive than the carrier flow path.

31. The implantable infusion apparatus of claim 17, wherein the medication flow path is less restrictive than the carrier flow path.

32. The implantable infusion apparatus of claim 17, wherein the carrier pump system has a carrier discharge rate and the medication discharge rate is greater than the carrier discharge rate.

33. The implantable infusion apparatus of claim 17, wherein the carrier pump system has a carrier discharge rate and the medication discharge rate is less than the carrier discharge rate.

34. The implantable infusion apparatus of claim 17, wherein the medication pump system and the carrier pump system comprises a power cell selected from the group consisting of a two-phase fluid power cell associated with the medication and the carrier reservoirs, the fluid in the power cell vaporizing at physiological temperatures and a gas pressurized power cell charged with a propellant.

35. The implantable infusion apparatus of claim 17, wherein the medication pump system and the carrier pump system comprises a battery operated system.

36. The implantable infusion apparatus of claim 17, further comprising a housing enclosing the implantable infusion apparatus wherein the housing is sized to be implantable in the human body.

37. The implantable infusion apparatus of claim 17, further comprising:
a medication access port to access the medication reservoir and covered with a medication compound septum; and
a carrier access port to access the carrier reservoir and covered with a carrier compound septum.

38. A method of infusing medication comprising:
storing a medication in a medication reservoir;
storing a carrier in a carrier reservoir, wherein the carrier reservoir is larger than the medication reservoir;
discharging the medication to a mixing chamber;
discharging the carrier to the mixing chamber;
mixing the medication with the carrier in the mixing chamber to dilute medication and form a medication/carrier mixture, wherein the mixing chamber is a micro fluidic chip having a capillary pathway disposed in a serpentine pattern;
discharging the diluted medication/carrier mixture; and
introducing a bolus dosage into the diluted medication/carrier mixture prior to discharging the diluted medication/carrier mixture.

39. The method of claim 38, further comprising:
restricting the discharge of the medication.

40. The method of claim 38, further comprising:
restricting the discharge of the carrier.

41. The method of claim 40, further comprising:
restricting the discharge of the medication.

42. The method of claim 41, further comprising:
restricting the discharge of the medication more than the discharge of the carrier.

43. The method of claim 41, further comprising:
restricting the discharge of the carrier more than the discharge of the medication.

44. The method of claim 38, wherein the mixing step comprises:
contacting the medication with the carrier in the mixing chamber;
flowing a contacted medication/carrier mixture through a series of mixing elements; and
delaying the discharging of the diluted medication/carrier mixture until the medication is diluted to the proper dosage.

45. A method of infusing medication comprising:
storing a medication in a medication reservoir;
storing a carrier in a carrier reservoir, wherein the carrier reservoir is larger than the medication reservoir;
controlling the discharge of the medication into a mixing chamber;
discharging the carrier into the mixing chamber;
mixing the medication with the carrier in the mixing chamber to dilute it to form a diluted medication/carrier mixture, wherein the mixing chamber is a micro fluidic chip having a capillary pathway disposed in a serpentine pattern;
discharging the diluted medication/carrier mixture; and
introducing a bolus dosage into the diluted medication/carrier mixture prior to discharging the diluted medication/carrier mixture.

46. The method of claim 45, further comprising:
restricting the discharge of the medication.

47. The method of claim 45, further comprising:
restricting the discharge of the carrier.

48. The method of claim 45, further comprising:
restricting the discharge of the medication.

49. The method of claim 48, further comprising:
restricting the discharge of the medication more than the discharge of the carrier.

50. The method of claim 48, further comprising:
restricting the discharge of the carrier more than the discharge of the medication.

51. The method of claim 45, wherein the mixing step comprises:
contacting the medication with the carrier in the mixing chamber;
flowing a contacted medication/carrier mixture through a series of mixing elements; and
delaying the discharging step until the medication is diluted to the proper dosage.

* * * * *